(12) United States Patent
Sander et al.

(10) Patent No.: US 11,571,172 B2
(45) Date of Patent: Feb. 7, 2023

(54) CIRCULAR-ARC-SHAPED HYBRID C-PROFILE FOR A C-ARM X-RAY APPARATUS

(71) Applicant: Ziehm Imaging GmbH, Nuremberg (DE)

(72) Inventors: Thomas Sander, Nuremberg (DE); Ewald Hauser, Nuremberg (DE)

(73) Assignee: Ziehm Imaging GmbH, Nuremberg (DE)

( * ) Notice: Subject to any disclaimer, the term of this patent is extended or adjusted under 35 U.S.C. 154(b) by 98 days.

(21) Appl. No.: 17/244,115

(22) Filed: Apr. 29, 2021

(65) Prior Publication Data

US 2021/0378610 A1    Dec. 9, 2021

(30) Foreign Application Priority Data

Jun. 4, 2020   (DE) ...................... 10 2020 003 363.6

(51) Int. Cl.
*A61B 6/00*   (2006.01)
*H05G 1/04*   (2006.01)

(52) U.S. Cl.
CPC .......... *A61B 6/4441* (2013.01); *A61B 6/4405* (2013.01); *H05G 1/04* (2013.01)

(58) Field of Classification Search
CPC .......... H05G 1/04; H05G 1/02; A61B 6/4405; A61B 6/4441; A61B 6/035; A61B 6/40; A61B 6/587; A61B 6/00; A61B 6/44; A61B 6/4476; A61B 6/56; A61B 2562/22; A61B 6/102; A61B 6/105; A61B 6/04; A61B 6/501; A61B 6/14; A61B 6/08; A61B 6/545; A61B 6/12; A61B 6/488; A61B 6/469; A61N 5/1081; H02G 11/00

USPC ......................................................... 378/193
See application file for complete search history.

(56) References Cited

U.S. PATENT DOCUMENTS

| | | | | |
|---|---|---|---|---|
| 4,955,046 A * | 9/1990 | Siczek | ................. | A61B 6/4441 |
| | | | | 378/197 |
| 6,132,087 A * | 10/2000 | Kusch | .................. | A61B 6/4405 |
| | | | | 378/197 |
| 9,220,471 B2* | 12/2015 | Noda | ................... | A61B 6/4233 |
| 2017/0202529 A1* | 7/2017 | Baumann | ............. | A61B 6/4476 |
| 2019/0008470 A1* | 1/2019 | Dirauf | .................. | A61B 6/4441 |
| 2021/0145383 A1* | 5/2021 | Barker | ................. | A61B 6/4441 |

FOREIGN PATENT DOCUMENTS

| | | |
|---|---|---|
| DE | 9218237 | 10/1993 |
| DE | 4214858 | 2/1994 |
| DE | 29802014 | 5/1998 |
| DE | 202011002199 | 4/2011 |
| DE | 102009054360 | 6/2011 |
| DE | 102010021657 | 12/2011 |
| DE | 202015008455 | 1/2016 |
| DE | 102016200442 | 7/2017 |
| DE | 102017211764 | 1/2019 |
| EP | 1372485 | 1/2004 |

\* cited by examiner

*Primary Examiner* — Irakli Kiknadze
(74) *Attorney, Agent, or Firm* — Knobbe Martens Olson & Bear, LLP

(57) ABSTRACT

The present technology relates to a circular-arc-shaped hybrid C-profile for a C-arm X-ray apparatus, said profile having a lightweight profile as the main body and a steel profile as a support profile for a bearing unit, the lightweight profile and the steel profile being connected to one another by connecting means.

19 Claims, 7 Drawing Sheets

CIRCULAR-ARC-SHAPED HYBRID C-PROFILE FOR A C-ARM X-RAY APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to medical imaging and more particularly to circular-arc-shaped profiles for a C-arm X-ray apparatus.

Description of the Related Art

C-arm X-ray devices have, on a chassis, a multi-adjustable holder having a bearing unit for a circular-arc-shaped C-arm, which is mounted in the bearing unit so as to be adjustable along the arm circumference, preferably by motor means, and which carries an X-ray source and an X-ray detector at its opposite ends. If such a C-arm X-ray unit is to be used to take projection images from which a 3D image data set can be reconstructed, the recording geometry of the projection images should be reproducibly determinable from the kinematics of the C-arm X-ray unit. For different orientations of the C-arm in space, the circular-arc shape of the C-arm should be changed as little as possible due to the torques that occur. A torque vector in the radial direction of the C-arm leads to torsion on the C-profile and thus to a deviation of the C-profile from the planar circular segment shape, and a torque vector perpendicular to the plane of the C-profile leads to an increase or decrease in the jaw width of the C-arm. For mobile C-arm X-ray units, it may also be necessary to find a compromise between the total mass of the C-arm and the rigidity thereof, because as the mass of the C-arm increases, the masses of the chassis and the bearing and adjustment elements of the C-arm X-ray unit also increase, which affects the maneuverability of the mobile C-arm X-ray unit.

A C-arm hollow profile having a rectangular cross section is known from document DE102010021657A, in which rollers mounted at an angle to the profile surfaces are provided.

Document DE102017211764A1 discloses a C-arm profile in which reinforcing profiles made of steel are cast in aluminum. The guide protrusions 8 of the cast aluminum profile, on which the track rollers engage, do not have reinforcements made of steel.

Document EP1372485B1 discloses an aluminum profile having steel reinforcements on the running surfaces, Document DE202015008455U1 discloses a hollow aluminum profile having a rectangular cross section, in which profile CFRP sheets are bonded to the outside of the profile outside the treads of the rollers.

Document DE102016200442A1 discloses a C-arm profile made of aluminum having inlaid steel wire races.

Document DE102016200442A1 discloses a C-arm profile which has a rectangular cross section made of aluminum with inlaid steel wire races, in which profile the planes of the track rollers are arranged obliquely to the boundary planes of the rectangular profile.

Document DE9218237U1 discloses an extruded profile having steel wire races for a C-arm.

Document DE4214858C1 discloses a CFRP profile having steel wire races.

Document DE202011002199U1 discloses a rectangular profile for a C-arm formed from 4 steel sheets welded together. Four additional steel sheets are welded to the rectangular profile to form running surfaces for the track rollers.

The applicant's document DE29802014U1 discloses a C-arm profile having clamped wire races and a hollow profile made of aluminum or fiber-reinforced plastic.

Document DE102009054360B4 discloses a groove for guiding an orbital drive belt in the convex outer surface of the C-arm.

SUMMARY

A problem addressed by embodiments of the present technology is that of creating a circular-arc-shaped C-profile for a C-arm X-ray apparatus, which profile has greater load resistance and torsional stiffness in comparison to known C-profiles.

This problem addressed by the present technology can be solved by a hybrid C-profile in which a steel profile providing the running surfaces for the orbital track rollers of a bearing unit is connected to a lightweight profile by connecting means.

The force lines of the forces introduced by the track rollers into the C-arm profile can run exclusively through a highly load-resistant material such as steel or stainless steel, which avoids the risk of deforming the light metal as in C-profiles known from the prior art having force lines running through the light metal.

The steel profile can be formed from a flat profile curved in the shape of a cylindrical casing and having running surfaces formed laterally. It is provided within the scope of the present technology to form the steel profile such that two annular retaining profiles protrude on the concave side.

The problems addressed by the present technology may be solved by an apparatus having a hybrid C-profile for a C-arm, in which the C-arm is movably guided along the periphery thereof on a support profile in a bearing unit, the hybrid C-profile comprising a main body having a circular-arc-shaped lightweight profile; and a support profile having a circular-arc-shaped steel profile, the support profile comprising a cylindrical casing-shaped portion having a convex side and a concave side, wherein first running surfaces are formed on the convex side, wherein second running surfaces for support rollers are formed on the concave side, and wherein a first lateral edge and a second lateral edge of the cylindrical casing-shaped portion comprise guide rails for guide rollers of the bearing unit, wherein the circular-arc-shaped lightweight profile and the circular-arc-shaped steel profile are connected to one another by connecting means. Advantageous embodiments are specified by the dependent claims.

It is provided to construct the C-profile as a hybrid component, in which a light metal profile as the main body is bonded form-fittingly, materially and/or frictionally to a supporting profile configured as a steel profile.

Forming the lightweight profile as a hollow profile is provided in the present technology. Furthermore, a U-shaped or V-shaped lightweight profile, open on the convex side thereof toward the steel profile, can be provided as the lightweight profile, and a hollow profile can be formed by covering the open lightweight profile with the steel profile. In order to stiffen the open U-shaped or V-shaped profile, first stiffeners 13, 13' forming chambers can be provided.

It is provided to use an extrusion-molded profile made from a light metal alloy, more particularly an aluminum or magnesium alloy, a die-cast or sand-cast profile made from aluminum or magnesium alloy, or a profile made from a fiber-reinforced or particle-reinforced plastic as the lightweight profile.

To improve the load-bearing ability and torsional stiffness, the lightweight profile can include internal planar stiffeners. The cross-sectional area of the lightweight profile can be adapted to the stress on the C-arm.

The steel profile made from a flat profile curved in the manner of a cylindrical casing can have a rectangular cross section forming running surfaces for support cylinder rollers and guide rollers for guidance.

It is provided to form the steel profile to have a cross section in the shape of the Greek letter pi, wherein the steel profile is formed from a flat profile curved in the shape of a cylindrical casing and having laterally formed running surfaces and two annular retaining profiles protruding, preferably orthogonally, on the concave side. It is also provided that the two retaining profiles are connected over their entire surface to a wall of the lightweight profile or that the retaining profiles are inserted as tongues into mating grooves of the lightweight profile and the tongue-and-groove joint is additionally fixed in a friction-fit, form-fit and/or materially bonded manner to form a hybrid C-profile.

It is provided that the steel profile is produced by forming processes from a flat material by bending, roll-milling, rolling and/or folding.

The flat material may be stamped and/or nibbled and/or laser-cut in the regions of the tongues to be formed.

The steel profile can be formed from a homogeneous steel or stainless steel material; however, it is also provided that the steel profile is formed from a clad steel and stainless steel material.

The lightweight profile and the steel profile can be connected by a material bond, for example by introducing an adhesive into the tongue-and-groove joints or by bonding mating surfaces of the lightweight profile and the steel profile. To prevent the cured adhesive from peeling off, the groove and/or the tongue and/or the mating surfaces of the lightweight profile and the steel profile can be profiled in the manner of an undercut, for example, by grooving or perforating or slitting the tongue or at least one mating surface. It is further provided that the bonding is a material bond, by means of soldering. It is further provided that the lightweight profile is form-fittingly connected to the steel profile by riveting, friction-welding riveting, nailing, screwing and/or pinning. It is also provided that the steel profile and the lightweight profile can be frictionally joined by pressing in the area of the groove in the lightweight profile. In addition, a combined use of different types of connection is also provided.

In the production of the C profile, it is provided that the steel profile is pressed onto the lightweight profile under elastic deformation by means of a holding apparatus for the lightweight profile and the steel profile is fixed to the lightweight profile after checking the dimensional accuracy of the hybrid C profile, in particular the dimensional accuracy with regard to the cylindrical-casing-shaped running surfaces.

DETAILED DESCRIPTION

The present technology will be explained in more detail with reference to the figures.

Figure 1:
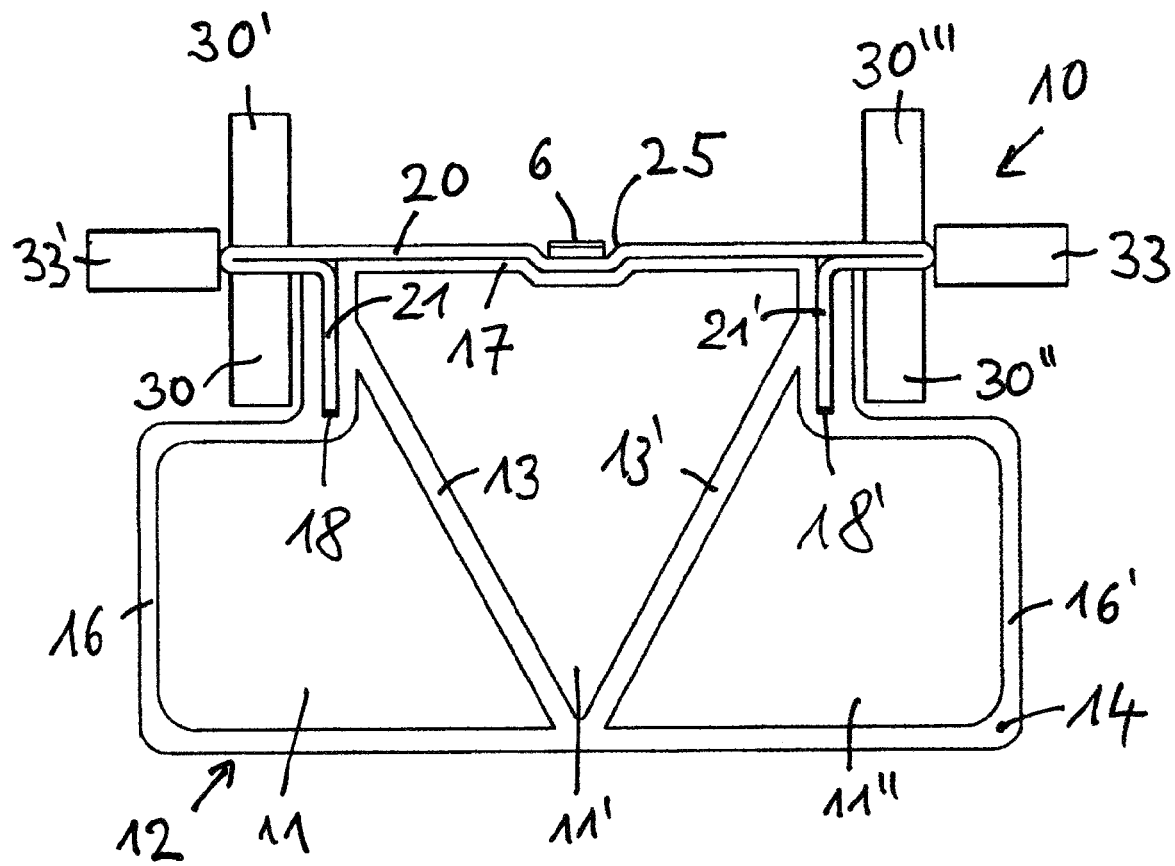
FIG. 1 illustrates a hybrid C-profile according to the present technology having support rollers.

FIG. 1 schematically shows an embodiment of a hybrid C-profile 10 having support rollers according to the present technology. The hybrid C-profile 10 can be formed from a lightweight profile 12 and a steel profile 20 by means of a non-detachable connection. The steel profile 20, which is preferably made of a flat material that is multiply folded, bent and rolled, has a first running surface 31, 31' and an opposite running surface 32, 32', cylindrical rollers 30, 30', 30", 30'" being mounted in a bearing unit, not shown, and rolling on the first and second running surfaces 31, 31', 32, 32' without play. To ensure freedom from play, the axles of the opposing cylindrical rollers 30, 30' and 30", 30'" are mounted in the bearing unit in such a way that the cylindrical rollers 30, 30', 30", 30'" hold the steel profile 20 with a sufficiently high contact pressure. For lateral guidance of the hybrid C profile 10, guide rollers 33, 33', whose axes are perpendicular to the first and second running surfaces 31, 31', 32, 32', engage at a first lateral edge and a second lateral edge running parallel thereto, of the steel profile 20. These guide rollers 33, 33' are preferably designed as profiled rollers. In the center of the convex, cylindrical region between the first running surfaces 31, 31', the steel profile 20 has a toothed belt guide groove 25, in which a toothed belt 6 is guided recessed in the region outside an omega drive, which is not shown.

Between the second running surfaces 32, 32', the steel profile 20 has two annular retaining profiles 22, 22' protruding orthogonally with respect to the first and second running surfaces 31, 31', 32, 32', which retaining profiles protrude as tongues 21, 21' into integrally formed grooves 18, 18' on the lightweight profile 12 during the connection of the steel profile 20 to the lightweight profile 12, the resulting tongue-and-groove joints being connected non-detachably to one another by additional connecting means such as an adhesive, riveted, soldered or welded joint.

A closed hollow profile having ducts 11, 11', 11" formed by first stiffeners 13, 13' and by a second stiffener 17 is provided as a lightweight profile 12 in the embodiment of FIG. 1. In addition to the tongue-and-groove joint, the lightweight profile 12 is connected to the steel profile 20 by a full-surface adhesive joint in the region of the second stiffener.

Channels 11, 11' and 11" are provided for the routing of energy supply lines and/or data and/or coolant lines, the outer contour of the lightweight profile 12 having sidewalls 16, 16' provided as a heat exchanger surface.

Figure 2:
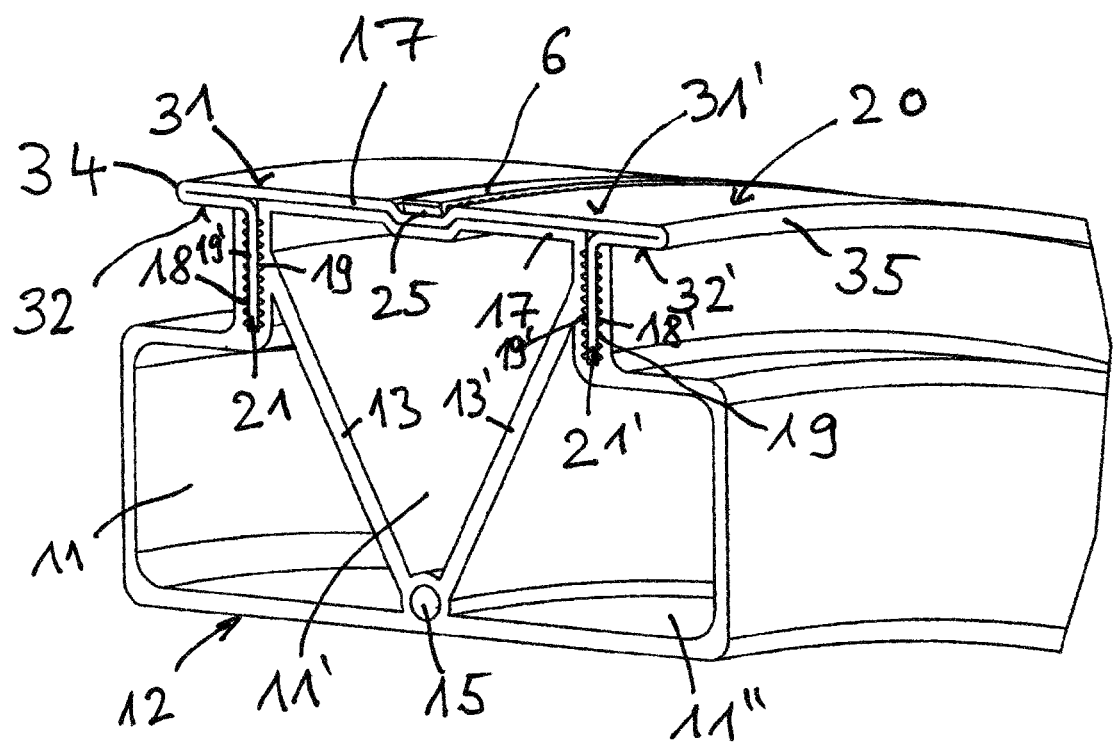
FIG. 2 is a perspective representation of a further embodiment of the hybrid C-profile according to the present technology, having a cooling duct.

FIG. 2 shows an additional embodiment of a hybrid C-profile 10 according to the present technology. The lightweight profile 12 here, in contrast to the lightweight profile 12 from FIG. 1, has an additional coolant duct 15, which has a good thermal contact with the outer surface of the lightweight profile 12 in the case where ductile light metal alloys are used for lightweight profile 12. The present technology provides that the number and quantity of the ducts can be varied. In the region of the grooves 18, 18' and the tongues 21, 21' of the tongue-and-groove joints, the undercuts 19, 19' for improving the adhesive bonding are shown schematically. If both the grooves 18, 18' and the tongues 21, 21' have undercuts, then an adhesive joint having a corrugated cross section is formed.

Figure 3:
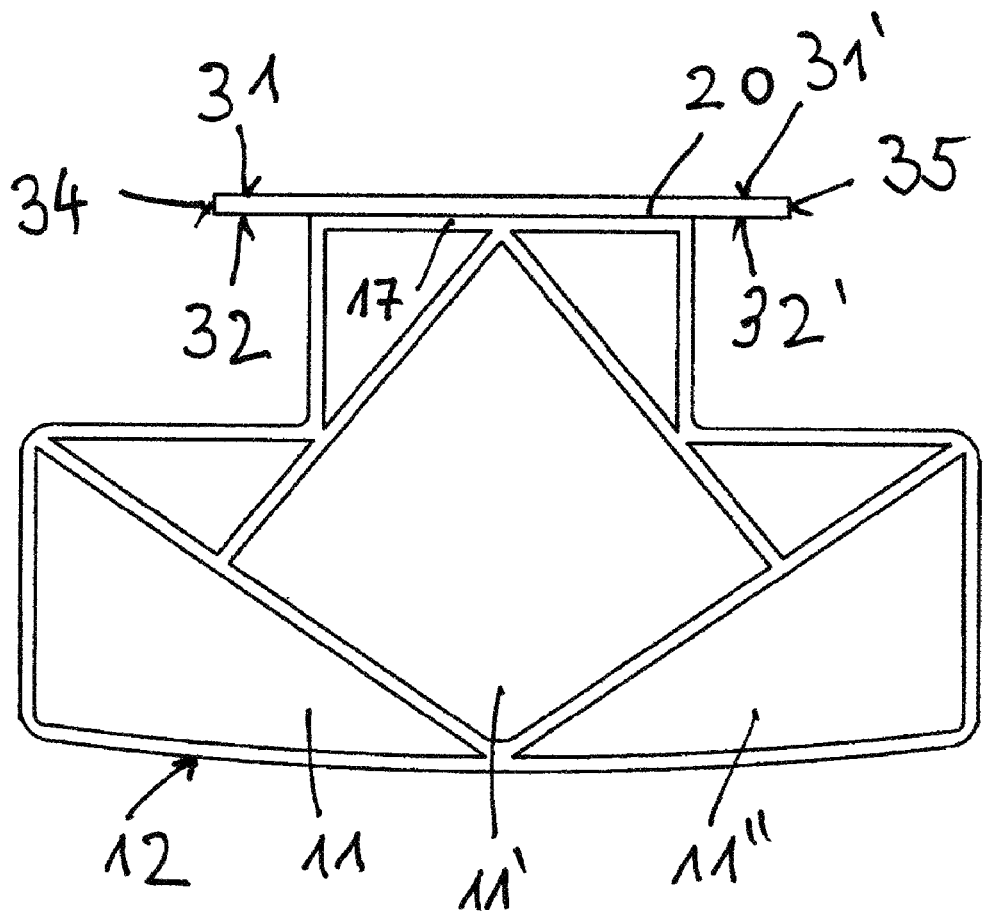
FIG. 3 illustrates an embodiment of a hybrid C-profile having a steel profile with a rectangular cross section.

FIG. 3 shows an embodiment of the connection of the steel profile 20 to the lightweight profile 12 in the region of the second stiffener 17. The cylindrical casing-shaped bent steel profile 12 having a rectangular cross section bears at the concave cylindrical casing-shaped surface thereof against the convex side of the lightweight profile 12 and is connected thereto by connecting means, not shown.

Figure 4:
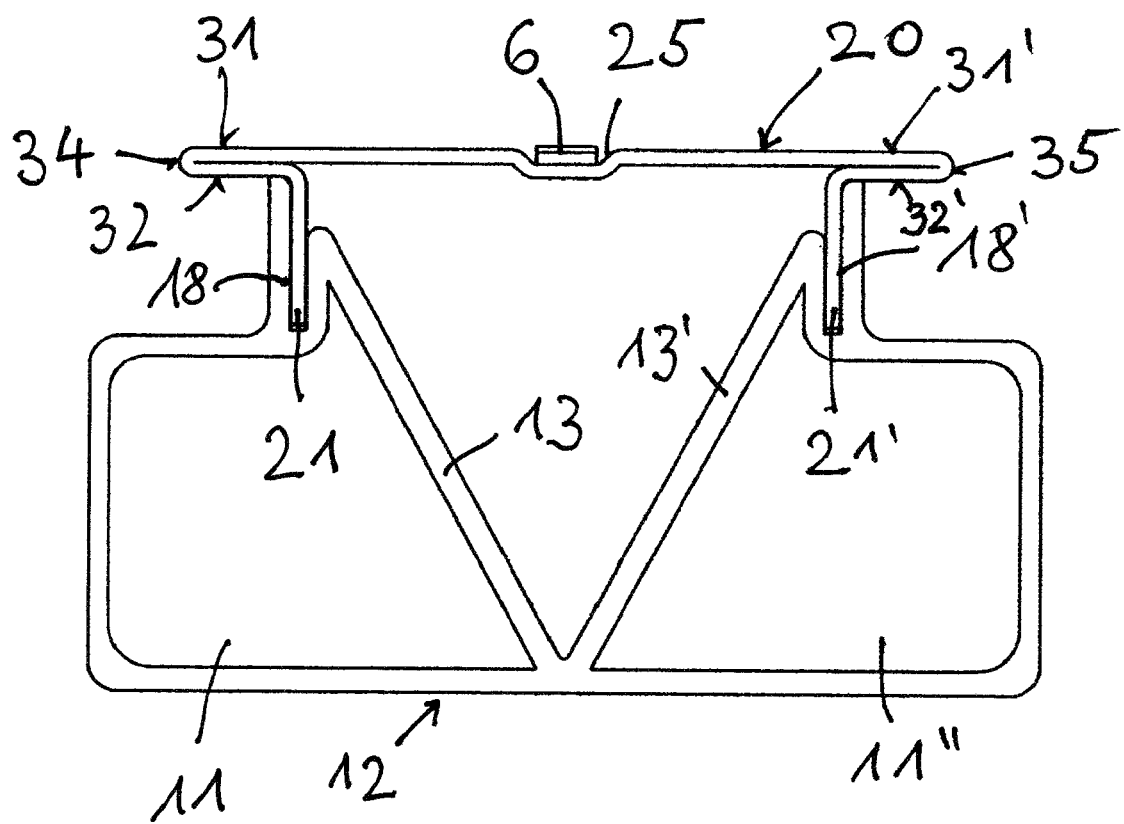
FIG. 4 illustrates a hybrid C-profile having a V-shaped lightweight profile and a tongue-and-groove connection.

The embodiment of FIG. 4 shows, as the lightweight profile 12, an open profile in the shape of a U-profile or a V-profile which is formed by omitting a second stiffener and has ducts 11, 11" formed by first stiffeners 13, 13'. By means of the tongue-and-groove joints 18, 21 and 18', 21' shown in FIG. 4 that connect the lightweight profile 12 to the steel profile 20, the open profile is covered by the steel profile (20), forming a closed hollow profile that forms a duct delimited by the lightweight profile 12 and the steel profile 20.

Figure 5:
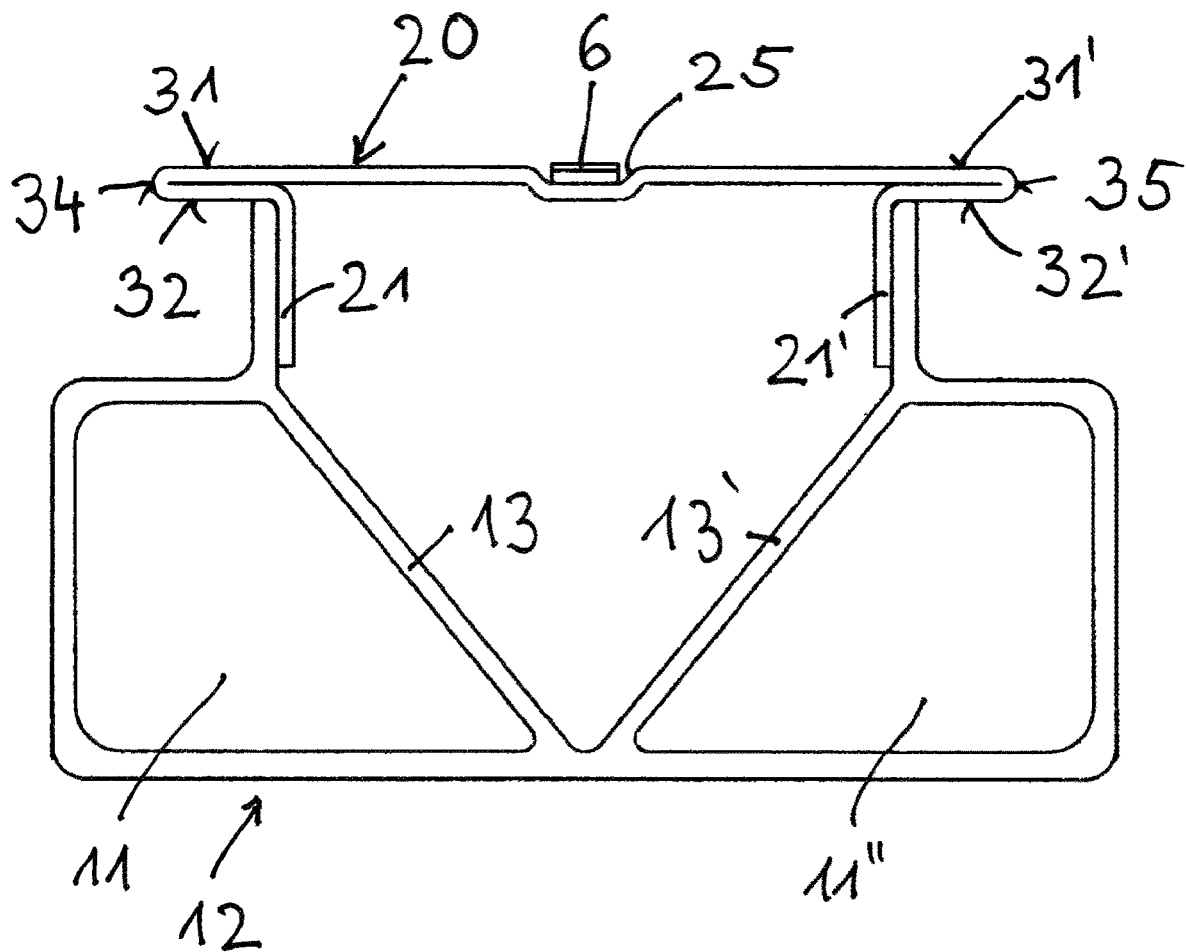
FIG. 5 illustrates a hybrid C-profile having a V-shaped lightweight profile and annular connecting points.

The embodiment of FIG. 5 shows, as the lightweight profile 12, an open U-profile or V-profile which is formed by omitting a second stiffener and has ducts 11, 11" formed by first stiffeners 13, 13'. The lightweight profile 12 is connected at annular faces of the lightweight profile to the steel profile 20 in the region of the annular tongues 21, 21' by means of connecting means that are not shown.

Figure 6:
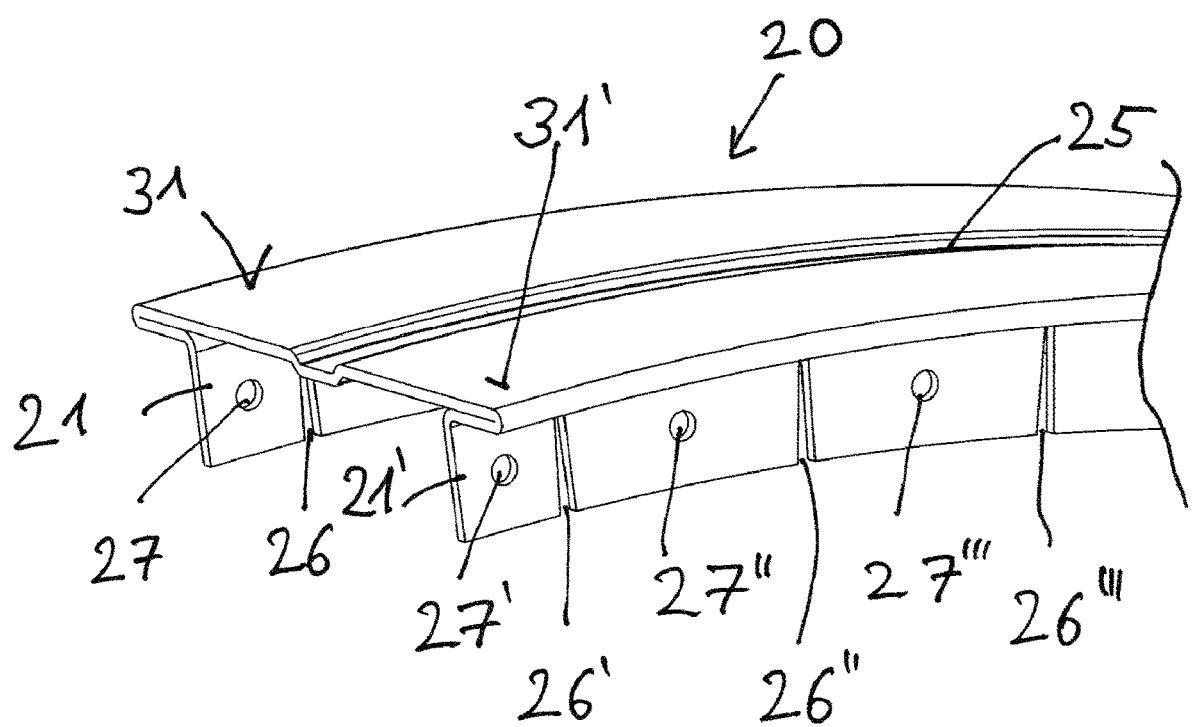
FIG. 6 illustrates embodiments for the shaping of the tongues.

FIG. 6 schematically represents an embodiment of a steel profile 20 according to the present technology. The tongues 21, 21' protruding, preferably orthogonally, from the running surfaces 31, 31' are provided, in order to improve the shaping of the steel profile 20, with slots 26, 26', 26", 26'" arranged orthogonally to the first running surfaces 31, 31'. The slots can be V-shaped with a broader opening on the sides of the tongues 21, 21' facing away from the running surfaces 31, 31'. Introducing recesses 27, 27', 27", 27'" on the tongues 21, 21' for better glue adhesion and/or producing form-fit connections after installation of the steel profile 20 is additionally provided.

Figure 7:
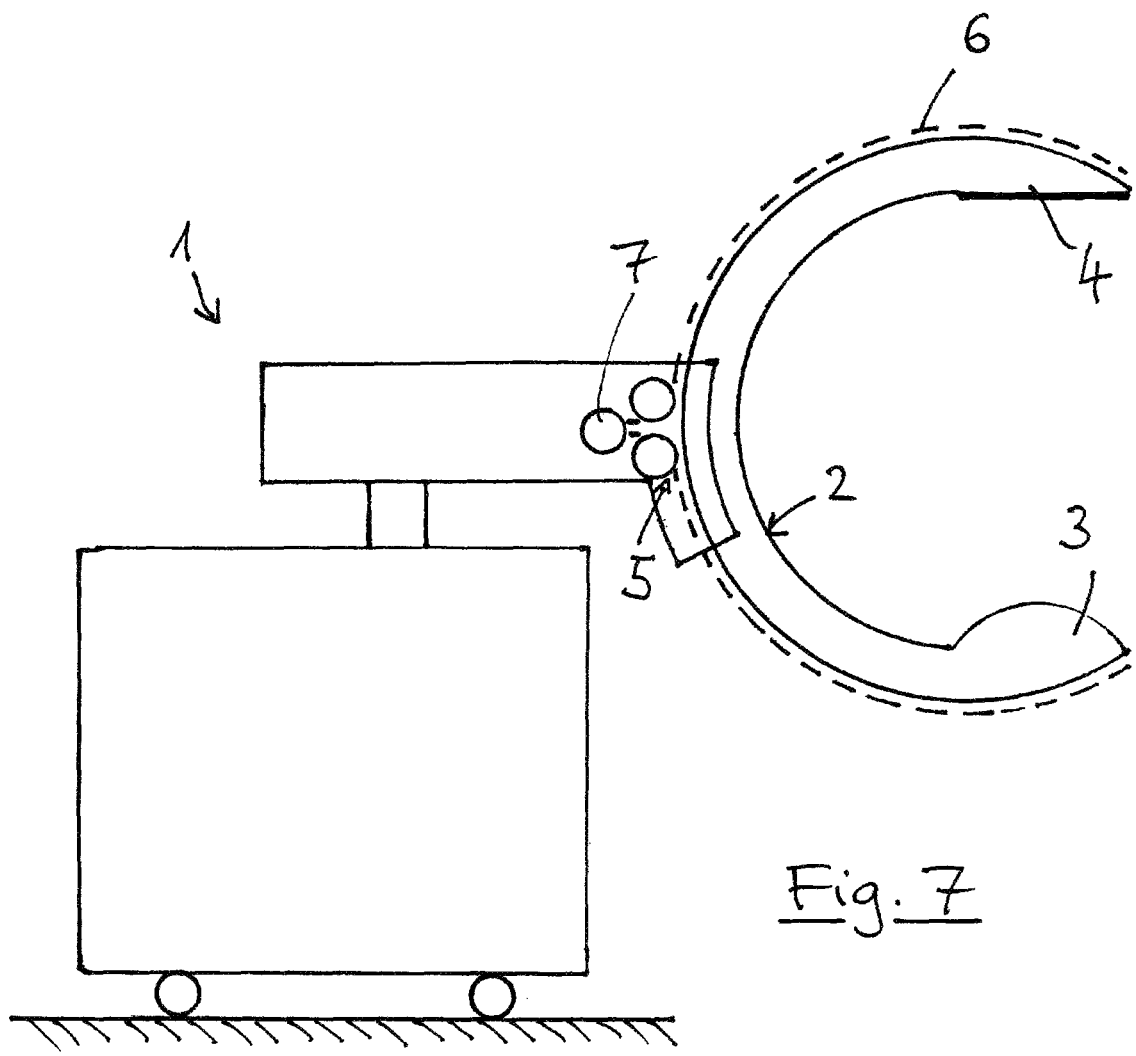
FIG. 7 illustrates a mobile C-arm X-ray apparatus.

FIG. 7 schematically represents a mobile C-arm X-ray apparatus 1 having a C-arm 2. The C-arm 2 is mounted movably along the periphery thereof on a multiply adjustable bearing unit 5. The C-arm 2 bears an X-ray source 3 at one end and a flat-panel X-ray detector (FPD) 4 at the opposing end. A schematically illustrated toothed belt 6, which runs on the convex side of the C-arm 2 from one end of the C-arm 2 to the other end thereof, is fixed to the convex side of the C-arm 2. In the interior of the bearing unit 5, the toothed belt 5 is tensioned and driven by means of an Omega drive 7. The Omega drive has a motor comprising a rotary encoder, by means of which the C-arm 2 can be reproducibly adjusted by motor means.

LIST OF REFERENCE NUMBERS

1 C-arm X-ray apparatus
2 C-arm
3 X-ray source
4 Flat panel detector (FPD)
5 Bearing unit
6 Toothed belt
7 Omega drive
10 Hybrid C-profile
11, 11', 11" Channel
12 Lightweight profile
13, 13' First stiffeners
14 Cross-sectional area
15 Coolant duct
16, 16' Side wall
17 Second stiffener
18, 18' Groove
19, 19' Undercut
20 Steel profile
21, 21' Tongue
22, 22' Retaining profile
25 Toothed belt guide groove
26, 26', 26", 26'", 26" Slot
27, 27', 27", 27'", 27" Recess
30, 30', 30", 30'" Cylinder roller
31, 31' First running surface
32, 32' Second running surface
33, 33' Guide roller
34 First lateral edge
35 Second lateral edge

What is claimed is:

1. A hybrid C-profile for a C-arm of a C-arm X-ray apparatus, in which the C-arm is movably guided along the periphery thereof on a support profile in a bearing unit, the hybrid C-profile comprising:
   a main body having a circular-arc-shaped lightweight profile; and
   a support profile having a circular-arc-shaped steel profile, the support profile comprising a cylindrical casing-shaped portion having a convex side and a concave side, wherein first running surfaces are formed on the convex side, wherein second running surfaces for support rollers are formed on the concave side, and wherein a first lateral edge and a second lateral edge of the cylindrical casing-shaped portion comprise guide rails for guide rollers of the bearing unit,
   wherein the circular-arc-shaped lightweight profile and the circular-arc-shaped steel profile are connected to one another by connecting means.

2. The hybrid C-profile of claim 1, wherein the lightweight profile has two circular-arc-shaped grooves, wherein the steel profile has two tongues protruding from the steel profile, and wherein the connecting means comprise tongue-and-groove joints between the grooves and the tongues.

3. The hybrid C-profile of claim 2, wherein the tongues run orthogonally to the first running surfaces and the second running surfaces.

4. The hybrid C-profile of claim 2, wherein the grooves and the tongues have at least one of grooves or profiled shapes on surfaces facing one another.

5. The hybrid C-profile of claim 1, wherein the lightweight profile is a hollow profile, and wherein an interior of the lightweight profile comprises first stiffeners and a second stiffener, forming ducts for receiving at least one of energy supply lines, data supply lines, and coolant supply lines.

6. The hybrid C-profile of claim 1, wherein the lightweight profile is open on a convex side thereof, the lightweight profile comprising first stiffeners, wherein the open convex side is covered by the steel profile, forming a closed hollow profile.

7. The hybrid C-profile of claim 1, wherein the lightweight profile comprises a light-metal alloy.

8. The hybrid C-profile of claim 7, wherein the light-metal alloy is an aluminum alloy.

9. The hybrid C-profile of claim 7, wherein the light-metal alloy is a magnesium alloy.

10. The hybrid C-profile of claim 1, wherein the lightweight profile comprises an extruded material.

11. The hybrid C-profile of claim 1, wherein the lightweight profile comprises at least one of fiber-reinforced composite plastic or particle-reinforced composite plastic.

12. The hybrid C-profile of claim 1, wherein the lightweight profile comprises a cast material.

13. The hybrid C-profile of claim 1, wherein the steel profile consists of steel.

14. The hybrid C-profile of claim 1, wherein the steel profile comprises stainless steel.

15. The hybrid C-profile of claim 1, wherein the steel profile comprises at least one of a bent, folded, roller profiled, stamped or laser cut flat material.

16. The hybrid C-profile of claim 1, wherein the steel profile comprises a convex surface on the convex side, the convex surface comprising a toothed belt guide groove for guiding a toothed belt in a center thereof between the first running surfaces.

17. The hybrid C-profile of claim 1, wherein the connecting means are materially bonded connections between the lightweight profile and the steel profile, the materially bonded connections comprising at least one of gluing, soldering or welding.

18. The hybrid C-profile of claim 1, wherein the connecting means are frictional connections between the lightweight profile and the steel profile produced by pressing together grooves of the lightweight profile.

19. The hybrid C-profile of claim 1, wherein the connecting means are form-fitting connections between the lightweight profile and the steel profile, the form-fitting connections comprising at least one of rivets, screws, nails, or pins.

* * * * *